(12) United States Patent
Fukai et al.

(10) Patent No.: US 7,587,025 B2
(45) Date of Patent: Sep. 8, 2009

(54) X-RAY ANALYSIS APPARATUS AND X-RAY ANALYSIS METHOD

(75) Inventors: Takayuki Fukai, Chiba (JP); Yoshiki Matoba, Chiba (JP); Kiyoshi Hasegawa, Chiba (JP)

(73) Assignee: SII NanoTechnology Inc., Chiba (JP)

( * ) Notice: Subject to any disclaimer, the term of this patent is extended or adjusted under 35 U.S.C. 154(b) by 0 days.

(21) Appl. No.: 11/972,337

(22) Filed: Jan. 10, 2008

(65) Prior Publication Data
US 2008/0212739 A1 Sep. 4, 2008

(30) Foreign Application Priority Data
Jan. 23, 2007 (JP) .............................. 2007-012620
Dec. 25, 2007 (JP) .............................. 2007-331546

(51) Int. Cl.
*G01N 23/201* (2006.01)
(52) U.S. Cl. ............................. 378/86; 378/44; 378/149
(58) Field of Classification Search ............. 378/44–50, 378/71–90, 145, 147, 149, 156–158
See application file for complete search history.

(56) References Cited

U.S. PATENT DOCUMENTS 4,393,512 A * 7/1983 Wang .......................... 378/156
5,365,563 A * 11/1994 Kira et al. ..................... 378/48

FOREIGN PATENT DOCUMENTS

JP 2004-150990 A 5/2004

* cited by examiner

*Primary Examiner*—Courtney Thomas
(74) *Attorney, Agent, or Firm*—Brinks Hofer Gilson & Lione (57) ABSTRACT

In an X-ray analysis apparatus and an X-ray analysis method, a quantitative analysis is stably performed by stably behaving an X-ray source. There are possessed an X-ray tubular bulb irradiating a primary X-ray to a sample, a primary X-ray adjustment mechanism capable of adjusting an intensity of the primary X-ray, an X-ray detector detecting a characteristic X-ray radiated from the sample, thereby outputting a signal including energy informations of the characteristic X-ray and a scattered X-ray, an analyzer analyzing the above signal, and an incident X-ray adjustment mechanism disposed between the sample and the X-ray detector, and capable of adjusting a total intensity of the characteristic X-ray and the scattered x-ray, which are entered to the X-ray detector.

6 Claims, 3 Drawing Sheets

X-RAY ANALYSIS APPARATUS AND X-RAY ANALYSIS METHOD

This application claims priority under 35 U.S.C. §119 to Japanese Patent Application Nos. JP2007-012620 filed Jan. 23, 2007 and JP2007-331546 filed Dec. 25, 2007, the entire content of which is hereby incorporated by reference.

BACKGROUND OF THE INVENTION

1. Field of the Invention

The present invention relates to an X-ray analysis apparatus and an X-ray analysis method, which are suitable for, e.g., an energy dispersive fluorescent X-ray analysis or the like.

2. Description of the Related Art

A fluorescent X-ray analysis is one in which a qualitative analysis or a quantitative analysis of a sample is performed by irradiating an X-ray emitted from an X-ray source to the sample and detecting, by an X-ray detector, a fluorescent X-ray which is a characteristic X-ray radiated from the sample, thereby obtaining a spectrum from an energy of the fluorescent X-ray. This fluorescent X-ray analysis is widely used in a process/quality control because it is possible to rapidly analyze the sample without being destructed. In recent years, there is contrived to increase a precision/sensitivity and thus a trace measurement becomes possible, so that there is expected a diffusion as an analysis technique performing especially a detection of a harmful substance contained in a material, a soil and the like.

As this analysis technique of the fluorescent X-ray analysis, there is a wavelength dispersion method in which the fluorescent X-ray is dispersed by a spectral crystal to thereby measure a wavelength and an intensity of the X-ray, an energy dispersion method in which the fluorescent X-ray is detected by a semiconductor detection element without being dispersed to thereby measure an energy and the intensity of the X-ray by a pulse height analyzer, or the like.

Hitherto, e.g., in JP-A-2004-150990 Gazette, there is disclosed a fluorescent X-ray analysis apparatus in which an element analysis of a measurement sample is performed by irradiating a primary X-ray to the measurement sample from an X-ray source through a primary filter, and detecting the fluorescent X-ray radiated from the measurement sample, which received the primary X-ray, by an X-ray detector.

In this fluorescent X-ray analysis apparatus, a reduction in background is contrived and an intensity adjustment of the fluorescent X-ray entering to the X-ray detector is performed by adjusting, by the primary filter, an intensity of the primary X-ray from the X-ray source by selecting a tube electric current of an X-ray tubular bulb and one from among the primary filters of plural kinds.

In the above prior art, the following problems are left.

In a conventional X-ray analysis apparatus, since there is a limitation on an ordinary operation range (maximum X-ray intensity capable of obtaining: maximum obtainable X-ray intensity) in the X-ray detector, there are performed a tube electric current adjustment of the X-ray tubular bulb used as the X-ray source and, as mentioned above by the primary filter, intensity adjustments of the fluorescent X-ray and a scattered X-ray, which enter to the X-ray detector. Here, since a detection lower limit in the X-ray analysis apparatus can be more improved the higher is the intensity of the fluorescent X-ray entered to the X-ray detector, it is set by an adjustment of an intensity of the primary X-ray to be irradiated so as to be capable of detecting approximately with the maximum obtainable X-ray intensity. However, depending on the measurement sample, there is a case where the fluorescent X-ray and the scattered X-ray, which enter to the X-ray detector, are too large and, additionally depending on a case, it is necessary to reduce the tube electric current of the X-ray tubular bulb till such a degree as to exceed an ordinary operation range of the X-ray tubular bulb and, by this, the intensity of the X-ray generating from the X-ray tubular bulb becomes unstable, so that there is an issue that the quantitative analysis by a calibration curve method or the like becomes difficult.

For example, hitherto, in a case where the maximum obtainable X-ray intensity of the X-ray detector is $20 \times 10^4$ cps (Counts Per Second) and the ordinary operation range of the X-ray tubular bulb is in a range from a maximum tube electric current value of 1000 µA to a minimum tube electric current value of 200 µA, if it is supposed that $10 \times 10^4$ cps is obtained at a tube electric current 20 µA in a rough measurement, in a main measurement the tube electric current is set to 40 µA, which is two times, in order to be coincided with the maximum obtainable X-ray intensity of the X-ray tubular bulb, and there is set such that the maximum obtainable X-ray intensity of $20 \times 10^4$ cps is obtained in the X-ray tubular bulb. In this case, the tube electric current does not arrive at the ordinary operation range of the X-ray tubular bulb, by this the intensity of the X-ray generating from the X-ray tubular bulb becomes unstable and, from the fact that, following upon it, an intensity of the detected X-ray becomes unstable, there is a disadvantage that the quantitative analysis is made difficult.

SUMMARY OF THE INVENTION

The present invention is one made in view of the above-mentioned problems, and its object is to provide an X-ray analysis apparatus and an X-ray analysis method, in each of which the quantitative analysis can be stably performed by causing a radiation source such as X-ray source to stably behave by being normally operated.

In order to solve the above problems, the present invention adopts the following constitution. That is, an X-ray analysis apparatus of the present invention possesses a radiation source irradiating a radiant ray to a sample; a radiant ray adjustment mechanism capable of adjusting an intensity of the radiant ray; an X-ray detector detecting a characteristic X-ray and a scattered X-ray, which are radiated from the sample, and outputting a signal including energy informations of the characteristic X-ray and the scattered X-ray; an analyzer analyzing the signal; and an incident X-ray adjustment mechanism disposed between the sample and the X-ray detector, and adjusting a total intensity of the characteristic X-ray and the scattered X-ray, which are entered to the X-ray detector.

In this X-ray analysis apparatus, since it possesses the radiant ray adjustment mechanism capable of adjusting the intensity of the radiant ray, and the incident X-ray adjustment mechanism disposed between the sample and the X-ray detector, and capable of adjusting the total intensity of the characteristic X-ray and the scattered X-ray, which are entered to the X-ray detector, a measurement becomes possible with a radiant ray irradiation power of the radiation source being brought about in maximum while considering a maximum obtainable X-ray intensity of the X-ray detector by adjusting both of an intensity of the radiant ray which is irradiated and the total intensity of the characteristic X-ray and the scattered X-ray, which are entered.

Further, in an X-ray analysis apparatus of the present invention, there is possessed a control section controlling the incident X-ray adjustment mechanism and the radiant ray adjustment mechanism such that the total intensity of the characteristic X-ray and the scattered X-ray, which are detected by the X-ray detector, is approximately a maximum obtainable X-ray intensity and an intensity of the radiant ray becomes within a normal operation range of a radiant ray irradiation power of the radiation source. That is, in this X-ray analysis apparatus, by the fact that the control section controls the incident X-ray adjustment mechanism and the radiant ray adjustment mechanism, thereby setting such that the total intensity of the characteristic X-ray and the scattered X-ray, which are detected by the X-ray detector, is approximately the maximum obtainable X-ray intensity and the intensity of the radiant ray becomes within the normal operation range of the radiant ray irradiation power of the radiation source, it is possible to easily obtain a stable radiant ray irradiation and a high characteristic X-ray intensity in the X-ray detector, so that there becomes such that the quantitative analysis can be stably performed.

Figure 5:
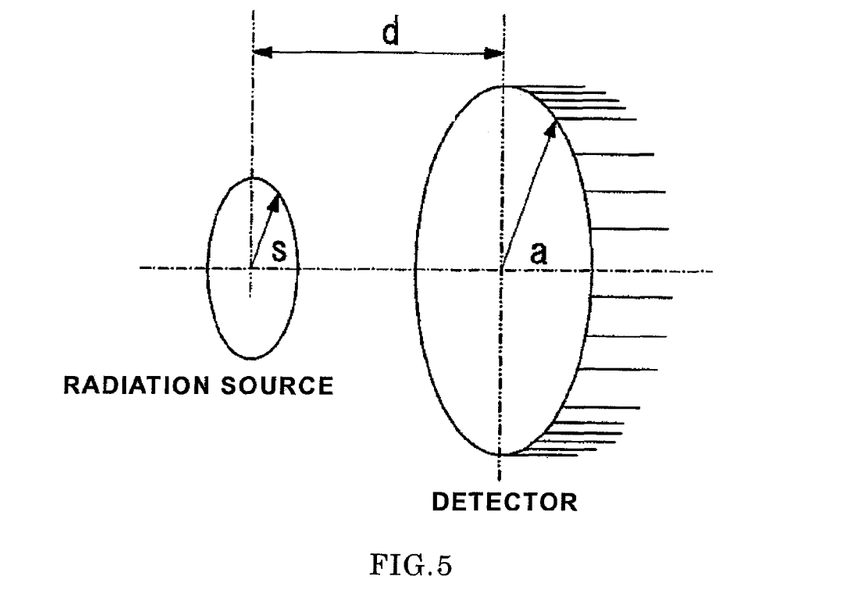
FIG. 5 is an explanatory view about a solid angle.

Further, in an X-ray analysis apparatus of the present invention, the X-ray detector has a detection face causing the characteristic X-ray and the scattered X-ray to enter, and the incident X-ray adjustment mechanism is a collimator capable of adjusting incident solid angles of the characteristic X-ray and the scattered X-ray in regard to the detection face. Here, generally, the solid angle means a portion marked off by a conical surface made by the fact that a half-line going out from the same point (apex of angle) on a space moves, and denotes an open degree of this conical surface. Concretely, it is defined as an area occupying on a surface in regard to a sphere whose radius is 1. Actually, each of the radiation source and the detector is not a point, and has a finite spread. As shown in FIG. 5, the solid angle, in a case where a disc-like radiation source and a disc-like detector are both placed perpendicularly to a common axis penetrating through centers of both, is calculated by a calculation expression like the below.

$$\Omega = \frac{4\pi a}{s} \int_0^\infty \frac{\exp(-dk)J_1(sk)J_1(ak)}{k} dk$$

s: radius of radiation source
a: radius of detector
d: distance between radiation source and detector
$J_1(x)$: Bessel function of x Further, a calculation of the solid angle can be found also by Monte Carlo simulation using random numbers.

In this X-ray analysis apparatus, as the incident X-ray adjustment mechanism, since there is adopted the collimator capable of adjusting the incident solid angle that the characteristic X-ray and the scattered X-ray, which generate from the sample, subtends the detection face, the characteristic X-ray and the scattered X-ray, which are entered to the detection face of the X-ray detector, are restricted in compliance with the incident solid angles of the characteristic X-ray and the scattered X-ray, so that their intensities can be easily adjusted.

Additionally, in an X-ray analysis apparatus of the present invention, the incident X-ray adjustment mechanism is an opening diameter alteration mechanism which has an X-ray incident hole causing the characteristic X-ray and the scattered X-ray to pass and enter to the detection face, and can alter to the X-ray incident hole of a different opening diameter. That is, in this X-ray analysis apparatus, since there is adopted the opening diameter alteration mechanism which can alter to the X-ray incident hole of the different opening diameter, the incident solid angles of the characteristic X-ray and the scattered X-ray can be easily altered by changing the opening diameter of the X-ray incident hole.

And, in an X-ray analysis apparatus of the present invention, the opening diameter alteration mechanism has the plural X-ray incident holes whose opening diameters mutually differ, and can arbitrarily dispose any one among the X-ray incident holes between the detection face and the sample. That is, in this X-ray analysis apparatus, since the opening diameter alteration mechanism arbitrarily selects and disposes one among the X-ray incident holes which are plurally prepared and whose opening diameters differ, it becomes possible to simply switch the incident solid angle by the fact that plural incident solid angles are previously prepared.

Further, in an X-ray analysis apparatus of the present invention, the incident X-ray adjustment mechanism has a position adjustment mechanism capable of adjusting an interval between the X-ray incident hole and the detection face. That is, in this X-ray analysis apparatus, since the interval between the X-ray incident hole and the detection face is altered by the position adjustment mechanism, even if the X-ray incident hole is only one, it is possible to continuously alter the incident solid angles of the characteristic X-ray and the scattered X-ray in compliance with the interval concerned, so that it becomes possible to highly, precisely adjust the total intensity of the characteristic X-ray and the scattered X-ray, which enter. Incidentally, if it is possible to arbitrarily select the plural X-ray incident holes whose opening diameter differ, a high degree of freedom in the alteration of the incident solid angle in a wider range can be obtained by an adjustment of the above interval by the position adjustment mechanism.

An X-ray analysis method of the present invention has a step of irradiating a radiant ray to a sample from a radiation source with an intensity of the radiant ray for a rough measurement, which is previously set; a step of detecting, by an X-ray detector, a rough measurement value that is a total intensity of a characteristic X-ray and a scattered X-ray, which are radiated from the sample; a step of performing a main measurement by adjusting, on the basis of the intensity of the radiant ray for the rough measurement and the rough measurement value, the intensity of the radiant ray by a radiant ray adjustment mechanism such that the total intensity of the characteristic X-ray and the scattered X-ray, which are detected by the X-ray detector, is approximately a maximum obtainable X-ray intensity and an intensity of the radiant ray becomes within a normal operation range of a radiant ray irradiation power of the radiation source, and adjusting a total intensity of the characteristic X-ray and the scattered X-ray, which are entered to the X-ray detector, by an incident X-ray adjustment mechanism disposed between the sample and the X-ray detector; a step of outputting a signal including energy informations of the characteristic X-ray and the scattered X-ray, that the X-ray detector obtains in the main measurement; and a step of analyzing the signal by an analyzer.

In this X-ray analysis method, by previously finding, by performing the above rough measurement, a relation under a default condition about levels of an intensity of an irradiated radiant ray and the total intensity of the characteristic X-ray and the scattered X-ray in the sample, in the main measurement, both of the intensity of the irradiated radiant ray and the total intensity of the characteristic X-ray and the scattered X-ray, which are entered to the X-ray detector, are adjusted by the radiant ray adjustment mechanism and the incident X-ray adjustment mechanism such that the total intensity of the characteristic X-ray and the scattered X-ray, which are detected by the X-ray detector, is approximately the maximum obtainable X-ray intensity and the intensity of the radiant ray becomes within the normal operation range of the radiant ray irradiation power of the radiation source. Accordingly, in the main measurement, since the radiant ray irradiation power is within the normal operation range, it is possible to obtain a stable radiant ray irradiation of the radiation source, so that there becomes so as to be capable of stably performing the quantitative analysis.

According to the present invention, the following advantage is brought about.

That is, according to the X-ray analysis apparatus and the X-ray analysis method, which are concerned with the present invention, since the intensity of the irradiated radiant ray is adjusted by the radiant ray adjustment mechanism and the total intensity of the characteristic X-ray and the scattered X-ray, which are entered to the X-ray detector, is adjusted by the incident X-ray adjustment mechanism, the measurement becomes possible with the radiant ray irradiation power of the radiation source being brought about in maximum while considering the maximum obtainable X-ray intensity of the X-ray detector, so that there becomes so as to be capable of stably performing the quantitative analysis.

DETAILED DESCRIPTION OF THE INVENTION

Figure 1:
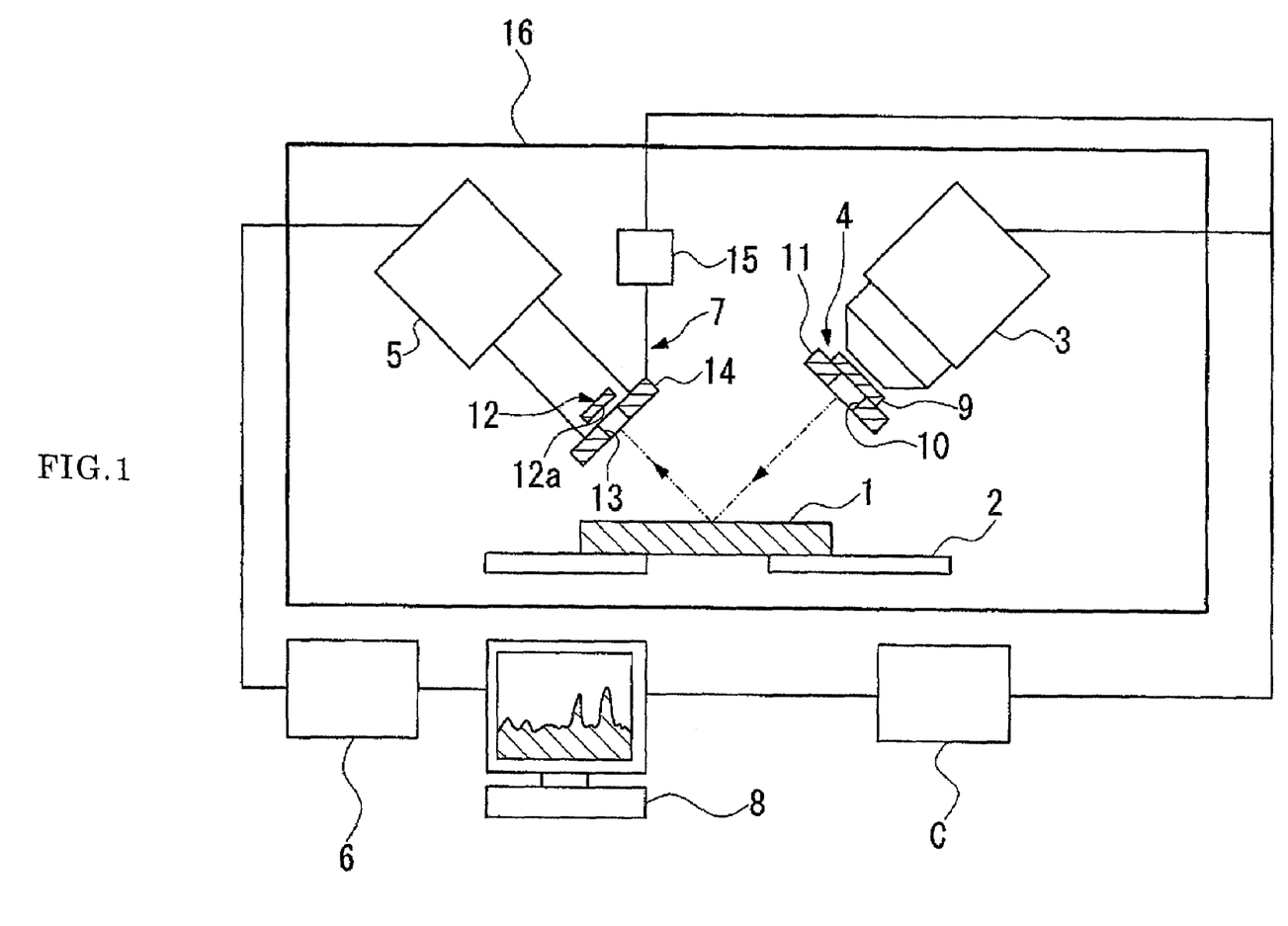
FIG. 1 is a schematic, whole constitutional view showing, in a first embodiment of an X-ray analysis apparatus and an X-ray analysis method, which are concerned with the present invention, the X-ray analysis apparatus.
Figure 2:
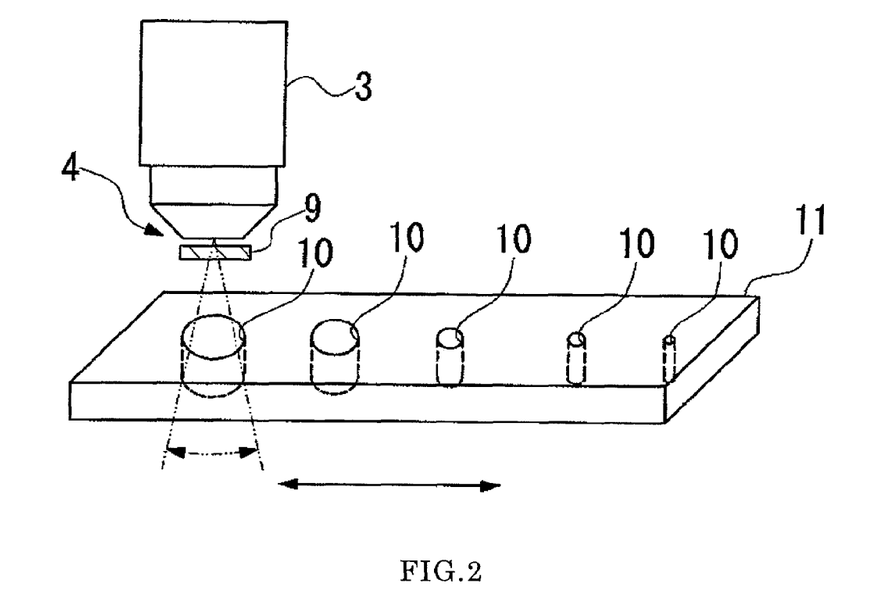
FIG. 2 is an explanatory view showing a positional relation between an emission side collimator and an X-ray tubular bulb in the first embodiment.
Figure 3:
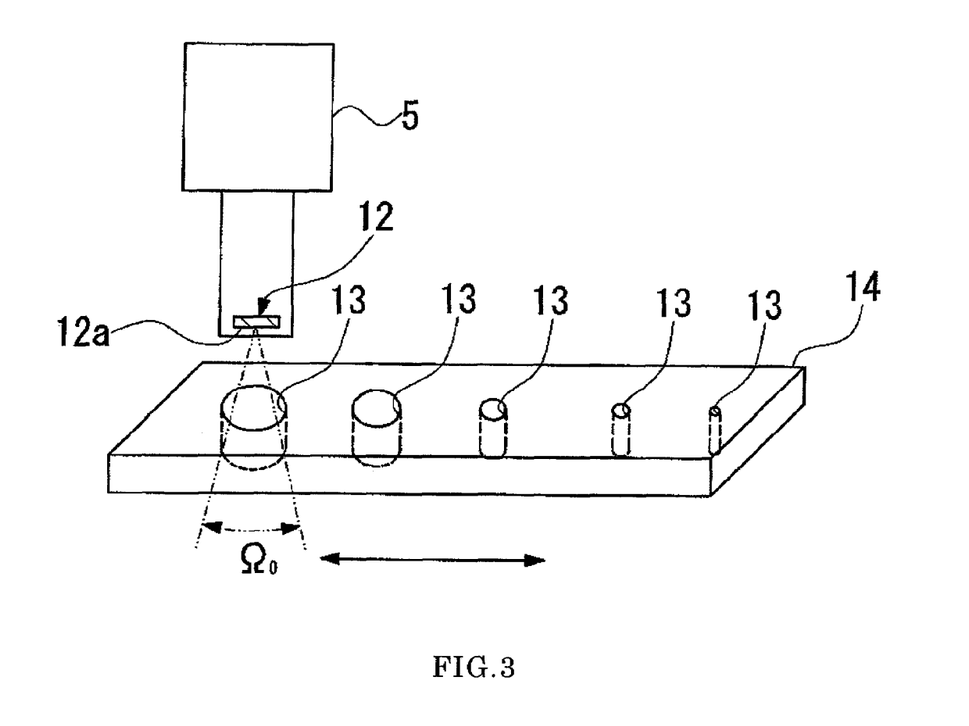
FIG. 3 is an explanatory view showing a positional relation between an incident side collimator and an X-ray detector in the first embodiment.

Hereunder, a first embodiment of an X-ray analysis apparatus and an X-ray analysis method, which are concerned with the present invention, is explained while referring to FIG. 1 to FIG. 3.

The X-ray analysis apparatus of the present embodiment is an energy dispersive fluorescent X-ray analysis apparatus and, as shown in FIG. 1 to FIG. 3, it possesses a sample stage 2 fixing a sample 1, an X-ray tubular bulb (radiation source) 3 irradiating a primary X-ray (radiant ray) to the sample 1, a primary X-ray adjustment mechanism (radiant ray adjustment mechanism) 4 capable of adjusting an intensity of the primary X-ray, an X-ray detector 5 detecting a characteristic X-ray and a scattered X-ray, which are radiated from the sample 1, and outputting a signal including energy informations of the characteristic X-ray and the scattered X-ray, an analyzer 6 connected to the X-ray detector 5 and analyzing the above signal, an incident X-ray adjustment mechanism 7 disposed between the sample 1 and the X-ray detector 5 and capable of adjusting a total intensity of the characteristic X-ray and the scattered X-ray, which are entered to the X-ray detector 5, a control section C controlling the primary X-ray adjustment mechanism 4 and the incident X-ray adjustment mechanism 7, and an analysis processing unit 8 connected to the analyzer 6 and the control section C.

The above sample stage 2 possesses a stepping motor (illustration omitted) by which a horizontal movement is made possible under a state in which the sample 1 is fixed, and the like.

The above X-ray tubular bulb 3 is one in which the X-ray, which is generated by the fact that thermoelectrons generated from a filament (positive electrode) in the tubular bulb are accelerated by a voltage applied between the filament (positive electrode) and a target (negative electrode) to thereby impinge against the target of W (tungsten), Mo (molybdenum), Cr (chromium) or the like, is emitted as the primary X-ray from a window of a beryllium foil or the like.

The above primary X-ray adjustment mechanism 4 can adjust a tube voltage and a tube electric current of the X-ray tubular bulb 3 and, as shown in FIG. 2, possesses a primary filter 9 attached to an X-ray emission face of the X-ray tubular bulb 3, an emission side collimator 11 disposed in front of the primary filter 9, i.e., between the primary filter 9 and the sample 1, and having plural X-ray emission holes 10 whose opening diameters differ, and an emission side collimator movement mechanism (illustration omitted) slidably moving the emission side collimator 11 in regard to the X-ray tubular bulb 3, thereby placing any one among the plural X-ray emission holes 10 in front of the primary filter 9. Incidentally, this emission side collimator 11 is constituted by a drive means such as stepping motor. Further, the primary filter 9 is a metal thin film or a metal thin plate of Cu (copper), Zr (zirconium), Mo (molybdenum) or the like, which is selected in compliance with the sample. Incidentally, the primary filter 9 is not one limited to one attached to the X-ray emission face of the X-ray tubular bulb 3, and there suffices if it exists between the X-ray tubular bulb 3 and the sample 1.

Further, in the present embodiment, although there is used the X-ray tubular bulb 3 whose normal operation range is 1000 µA to 200 µA, it is not one limited to this.

The above X-ray detector 5 possesses a semiconductor detection element 12 disposed with its detection face 12a being directed to an incident window of the X-ray. This semiconductor detection element 12 is a Si (silicon) element which is a pin-structure diode, and one which, if one X-ray photon enters, generates an electric current pulse corresponding to this one X-ray photon. A momentary electric current value of this electric current pulse is proportional to an energy of the characteristic X-ray which enters. Further, the X-ray detector 5 is set such that the electric current pulse generated in the semiconductor element 12 is converted into and amplified to a voltage pulse, and outputted as a signal.

Incidentally, in the present embodiment, although there is used the X-ray detector 5 whose maximum obtainable X-ray intensity is $20 \times 10^4$ cps (Counts Per Second), it is not limited to this.

The above analyzer 6 is a pulse height analyzer (multichannel pulse-height analyzer) which obtains a pule height of the voltage pulse from the above signal, thereby forming an energy spectrum.

As shown in FIG. 3, the above incident X-ray adjustment mechanism 7 is an opening diameter alteration mechanism having plural X-ray incident holes 13 which cause the X-ray to pass and enter to the detection face 12a, and can alter to the X-ray incident hole 13 of a different opening diameter.

That is, the incident X-ray adjustment mechanism 7 possesses an incident side collimator 14 disposed in front of the detection face 12a of the semiconductor detection element 12 in the X-ray detector 5, i.e., between the detection face 12a and the sample 1, and having the plural X-ray incident holes 13 whose opening diameters differ, and an incident side collimator movement mechanism 15 slidably moving an incident side collimator 14 in regard to the X-ray detector 5, thereby arbitrarily placing any one among the plural X-ray incident holes 13 in front of the detection face 12a, i.e., between the detection face 12a and the sample. Like this, the incident X-ray adjustment mechanism 7 is a collimator capable of adjusting incident solid angles of the characteristic X-ray and the scattered X-ray in regard to the detection face 12a by selecting one from among the plural X-ray incident holes 13 whose opening diameter differ. Incidentally, this incident side collimator movement mechanism 15 is constituted by the drive means such as stepping motor. Additionally, between the sample 1 and the detection face 12a, there exists also one in which a secondary filter (illustration omitted) is attached for the purpose of reducing the scattered X-ray generated from the sample 1. The secondary filter is a metal thin film or a metal thin plate of Ni (nickel) or the like, which is selected in compliance with the sample.

The above control section C has a processing circuit controlling the incident X-ray adjustment mechanism 7 and the primary X-ray adjustment mechanism 4 such that a total intensity of the characteristic X-ray and the scattered X-ray, which are detected by the X-ray detector 5, is approximately the maximum obtainable X-ray intensity, and the intensity of the primary X-ray becomes within a normal operation range of a primary X-ray irradiation power of the X-ray tubular bulb 3. Further, the control section C controls the tube electric current of the X-ray tubular bulb 3.

The above analysis processing unit 8 is a computer constituted by a CPU or the like, and made so as to display an energy spectrum sent from the analyzer 6 to a display, and be capable of inputting/setting the maximum obtainable X-ray intensity, the tube electric current of the X-ray tubular bulb 3, the normal operation range of the X-ray irradiation power, and the like to the above control section C. Incidentally, the above control section C may be provided in the processing circuit within the analysis processing unit 8.

The sample stage 2, the X-ray tubular bulb 3, the primary X-ray adjustment mechanism 4, the X-ray detector 5 and the incident X-ray adjustment mechanism 7 are accommodated in a sample chamber 16 capable of being depressurized, and there is made such that an inside of the sample chamber 16 is depressurized at a measurement time such that the X-ray is not absorbed to an atmosphere in the air.

Next, there is explained about an X-ray analysis method using the X-ray analysis apparatus of the present embodiment.

First, under a default condition for the rough measurement, which is previously set, the primary X-ray is irradiated to the sample 1 from the X-ray tubular bulb 3. That is, the primary X-ray is irradiated to the sample 1 at the tube electric current (e.g., 20 μA) for the rough measurement from the X-ray emission hole 10 and the X-ray incident hole 13, whose opening diameters are previously set, and the X-ray tubular bulb 3. And, the characteristic X-ray and the scattered X-ray, which are radiated from the sample 1, are detected by the X-ray detector 5 in a short time (e.g., 2 seconds), and an electric current pulse generated in the semiconductor detection element 12 is converted into and amplified to a voltage pulse, thereby outputting as a signal.

Next, the energy spectrum in the rough measurement is formed by selecting the signal from the X-ray detector 5 to the X-ray intensity for every energy by the detector 6.

Next, on the basis of the default condition of the rough measurement, which is obtained through the analysis processing unit 8, and a total intensity of the characteristic X-ray and the scattered X-ray in the rough measurement, which are obtained by the analyzer 6, the control section C adjusts the intensity of the primary X-ray by the primary X-ray adjustment mechanism 4 so as to satisfy a condition in which a total intensity of the characteristic X-ray and the scattered X-ray, which are detected by the X-ray detector 5, is approximately the maximum obtainable X-ray intensity and the intensity of the primary X-ray becomes within the ordinary operation range of the primary X-ray irradiation power of the X-ray tubular bulb 3, and adjusts a total intensity of the characteristic X-ray and the scattered X-ray, which are entered to the X-ray detector 5, by the incident X-ray adjustment mechanism 7.

That is, on the basis of the total intensity of the characteristic X-ray and the scattered X-ray in the rough measurement, there are calculated optimum conditions of the opening diameter of the X-ray emission hole 10, the tube electric current of the X-ray tubular bulb 3 and the opening diameter of the X-ray incident hole 13, which satisfy the above condition. Additionally, by the primary X-ray adjustment mechanism 4 and the incident X-ray adjustment mechanism 7, the emission side collimator 11 and the incident side collimator 14 are moved, thereby disposing the X-ray emission hole 10 and the X-ray incident hole 13, which correspond to the optimum conditions and are selected, respectively in predetermined positions. Additionally, by the control section C, the X-ray tubular bulb 3 is set to a calculated tube electric current. And, the main measurement is performed in accordance with these optimum conditions.

The above optimum conditions are calculated on the basis of an information of the rough measurement such that the incident X-ray intensity equivalent to the maximum obtainable X-ray intensity of the X-ray detector 5 is realized by the X-ray incident hole 13 whose opening diameter is as small as possible. In a method of this calculation, first, from a ratio between an incident solid angle in the opening diameter of the X-ray incident hole 13 under the above default condition and an incident solid angle in the opening diameter of the X-ray incident hole 13 other than the former, and the total intensity of the characteristic X-ray and the scattered X-ray in the rough measurement, a theoretical value, of the total intensity of the characteristic X-ray and the scattered X-ray, for every X-ray incident hole 13 in the tube electric current for the rough measurement is calculated as follows.

$$I_0 \times (\Omega_k / \Omega_0)$$

($I_0$: total intensity of characteristic X-ray and scattered X-ray under default condition)

($\Omega_0$: incident solid angle in X-ray incident hole 13 of opening diameter+$\phi_0$ under default condition)

($\Omega_k$: incident solid angle in X-ray incident hole 13 of opening diameter $\phi_k$ in main measurement)

Additionally, there is calculated a total intensity of the characteristic X-ray and the scattered X-ray, which are entered to the X-ray detector 5 when the tube electric current of the X-ray tubular bulb 3 is used at a maximum rating. Here, it is supposed that the total intensity of the characteristic X-ray and the scattered X-ray is directly proportional to the tube electric current. During a value of this exceeds the maximum obtainable X-ray intensity of the X-ray detector 5, the X-ray incident hole 13 whose opening diameter is smallest is selected as for the main measurement.

Incidentally, if it is supposed that a distance between the sample and the detection face 12a is constant, an incident solid angle $\Omega$ in this X-ray analysis apparatus is found with an opening diameter $\phi$ of the X-ray incident hole 13, a thickness h of the X-ray incident hole, an interval d between the X-ray incident hole 13 and the detection face 12a, and a diameter S of the detection face 12a being made a function. Here, if the interval d between the X-ray incident hole 13 and the detection face 12a, the thickness h of the X-ray incident hole, and the diameter S of the detection face 12a are constant, the incident solid angle Ω becomes the function of the opening diameter φ of the X-ray incident hole 13.

In a case where the opening diameters of the respective X-ray incident angles are set from $\phi_0$ till $\phi_k$ ($\phi_0 > \phi_1 > \ldots > \phi_k$), there is found the minimum opening diameter $\phi_k$ satisfying $$I_{max} \leq 10 \times (\phi_k/\phi_0) \times (i_{max}/i_0)$$

($I_{max}$: maximum obtainable X-ray intensity)

($I_0$: total intensity of characteristic X-ray and scattered X-ray under default condition)

($\Omega_0$: Incident Solid Angle in X-Ray Incident hole 13 of opening diameter $\phi_0$ under default condition)

($\Omega_k$: incident solid angle in X-ray incident hole 13 of opening diameter $\phi_k$ in main measurement)

($i_0$: tube electric current under default condition)

($i_{max}$: maximum rating of tube electric current).

Here, in the incident solid angle ratio $\Omega_k/\Omega_0$, a calculated value is previously incorporated by a constant. The tube electric current i is adjusted so as to become $$I_{max} = I_0 \times (\Omega_k/\Omega_0) \times (i/i_0).$$

Here, even for a greatest one among the X-ray incident holes 13, in a case where the above condition for optimizing the opening diameter is not satisfied, for the X-ray incident hole 13 there is used the greatest one, and for the tube electric current there is used the maximum rating.

Incidentally, in a case where the X-ray detector 5 is a silicon drift detector (SSD) or the like, when the total intensity of the characteristic X-ray and the scattered X-ray, which enter, is the same, since a peak back ratio, which is a rate between a peak intensity of an object detection element by the characteristic X-ray and a background intensity by the scattered X-ray, becomes better the smaller is the opening diameter of the X-ray incident hole 13, it is possible to contrive an improvement in a detection lower limit, so that it becomes possible to perform a measurement of higher precision.

Concretely, e.g., in a case where the maximum obtainable X-ray intensity of the X-ray detector 5 is $20 \times 10^4$ cps and the normal operation range of the X-ray tubular bulb 3 is 200-1000 μA, if it is supposed that $10 \times 10^4$ cps is obtained at the tube electric current 20 μA of the X-ray tubular bulb 3 by using the X-ray incident hole 13 whose opening diameter is greatest as the default condition of the rough measurement, as to the opening diameter of the optimum X-ray incident hole 13 there is selected one of a smallest opening diameter among ones satisfying $$20 \times 10^4 \leq 10 \times 10^4 \times (\Omega_k/\Omega_0) \times (1000 \ \mu A/20 \ \mu A).$$

And, e.g., in a case where the ratio ($\Omega_k/\Omega_0$), of the incident solid angle, between the smallest opening diameter $\phi_k$ and the opening diameter $\phi_0$ under the default condition is 0.05, the tube electric current is determined as 800 μA from $$20 \times 10^4 = 10 \times 10^4 \times 0.05 \times (i/20).$$

By this, in the main measurement, it is possible to obtain the maximum obtainable X-ray intensity of $20 \times 10^4$ cps in the X-ray detector 5. Incidentally, although it is desirable to set the condition so as to coincide with the maximum obtainable X-ray intensity, there may be a value near the maximum obtainable X-ray intensity, which can be said approximately the maximum obtainable X-ray intensity.

In the main measurement which is set to the optimum condition like this, the energy spectrum is displayed in the analysis processing unit 8 by outputting a signal including energy informations of the characteristic X-ray and the scattered X-ray, that the X-ray detector 5 obtains, and additionally sending the energy spectrum obtained by analyzing this signal by the analyzer 6 to the analysis processing unit 8.

Incidentally, in the main measurement, as a predetermined measurement time, there was measured with 100 seconds for instance in order to obtain the sufficient energy informations.

In the present embodiment, since there are possessed the primary X-ray adjustment mechanism 4 capable of adjusting the intensity of the primary X-ray, and the incident X-ray adjustment mechanism 7 which is disposed between the sample 1 and the X-ray detector 5 and can adjust the total intensity of the characteristic X-ray and the scattered X-ray, which are entered to the X-ray detector 5, the measurement becomes possible with the X-ray irradiation power of the X-ray tubular bulb 3 being brought about in maximum while considering the maximum obtainable X-ray intensity of the X-ray detector 5 by adjusting both of the intensity of the primary X-ray which is irradiated and the total intensity of the characteristic X-ray and the scattered X-ray, which are entered. Accordingly, in the main measurement, since the radiant ray irradiation power is within the normal operation range, it is possible to obtain a stable radiant ray irradiation of the radiation source, so that the quantitative analysis can be stably performed.

Concretely, the control section C controls the incident X-ray adjustment mechanism 7 and the primary X-ray adjustment mechanism 4 including a tube electric current adjustment and, by setting such that the total intensity of the characteristic X-ray and the scattered X-ray, which are detected by the X-ray detector 5, is approximately the maximum obtainable X-ray intensity and the intensity of the primary X-ray becomes within the normal operation range of the primary X-ray irradiation power of the X-ray tubular bulb 3, it is possible to easily obtain a stable primary X-ray irradiation and a high characteristic X-ray intensity in the X-ray detector 5.

Especially, as the incident X-ray adjustment mechanism 7, since there is adopted the incident side collimator 14 capable of adjusting incident solid angles of the characteristic X-ray and the scattered X-ray in regard to the detection face 12a of the X-ray detector 5 by altering the X-ray incident hole 13 of the different opening diameter, the characteristic X-ray entering to the detection face 12a of the X-ray detector 5 is limited in compliance with the incident solid angles of the characteristic X-ray and the scattered X-ray, so that the intensity of the characteristic X-ray can be easily adjusted.

Figure 4:
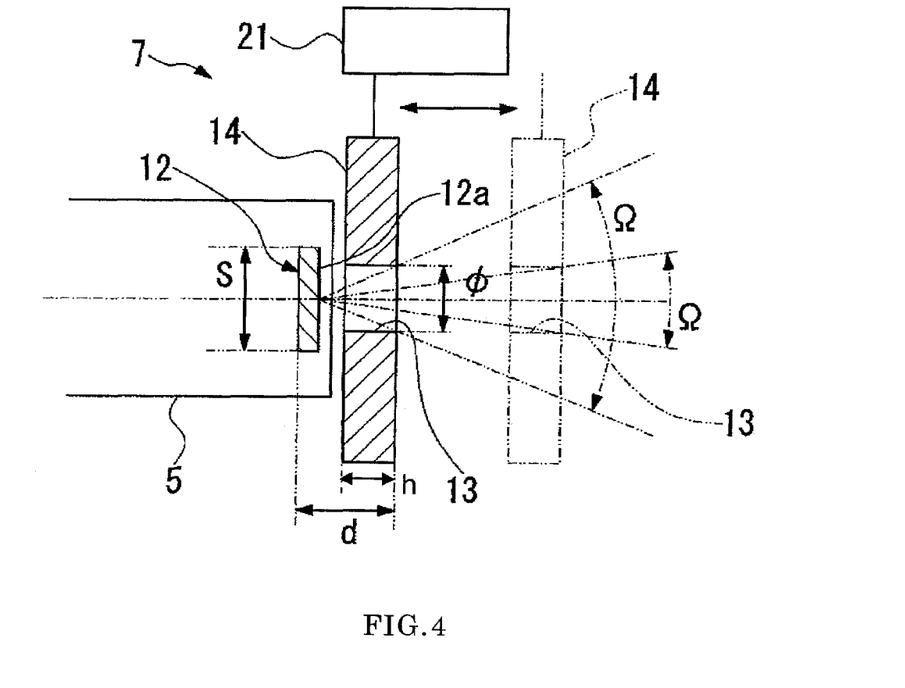
FIG. 4 is an explanatory view showing a positional relation between an X-ray detector and an incident side collimator in a second embodiment of an X-ray analysis apparatus and an X-ray analysis method, which are concerned with the present invention.

Next, there is explained about a second embodiment of the X-ray analysis apparatus and the X-ray analysis method, which are concerned with the present invention, while referring to FIG. 4. Incidentally, in the following explanations of the embodiment, the same reference or sign is applied to the same constitutional element as explained in the above-mentioned embodiment, and its explanation is omitted.

A different point between the second embodiment and the first embodiment exists in a point that, in the first embodiment, the incident X-ray adjustment mechanism 7 selects, among the plural X-ray incident holes 13 whose opening diameters differ, one coinciding with the condition to thereby use it in the main measurement, whereas, in the X-ray analysis apparatus of the second embodiment, the incident X-ray adjustment mechanism 7 has, as shown in FIG. 4, a position adjustment mechanism 21 capable of adjusting the interval d between the X-ray incident hole 13 and the detection face 12a of the X-ray detector 5.

That is, the X-ray analysis apparatus of the second embodiment has the position adjustment mechanism 21 moving the incident side collimator 14, in which there is formed the X-ray incident hole 13, so as to be capable of approaching to or separating from the detection face 12a of the X-ray detector 5. As mentioned above, if it is supposed that the distance between the sample and the detection face 12a is constant, the incident solid angle Ω in this X-ray analysis apparatus is found with the opening diameter φ of the X-ray incident hole 13, the interval d between the X-ray incident hole 13 and the detection face 12a, the thickness h of the X-ray incident hole, and the diameter S of the detection face 12a being made the function. Accordingly, if the opening diameter φ of the X-ray incident hole 13, the thickness h of the X-ray incident hole, and the diameter S of the detection face 12a are constant, the incident solid angle Ω becomes the function of the interval d between the X-ray incident hole 13 and the detection face 12a.

In this second embodiment, by being made similar to the first embodiment, the incident solid angle Ω of the optimum condition is found by the rough measurement, thereby calculating the interval d between the X-ray incident hole 13 and the detection face 12a, which corresponds to this incident solid angle Ω. The control section C causes the incident side collimator 14 to move so as to become the calculated interval d by the position adjustment mechanism 21, thereby setting a position of the X-ray incident hole 13 in regard to the detection face 12a.

Like this, in the second embodiment, since the interval d between the X-ray incident hole 13 and the detection face 12a is altered by the position adjustment mechanism 21, even if the X-ray incident hole 13 is only one, the incident solid angles Ω of the characteristic X-ray and the scattered X-ray can be continuously altered in compliance with the interval d concerned, so that it becomes possible to highly, precisely adjust the total intensity of the characteristic X-ray and the scattered X-ray, which enter. Incidentally, similarly to the first embodiment, if the plural X-ray incident holes 13 whose opening diameters differ are arbitrarily selected, the alteration of the incident solid angle Ω becomes possible in a wider range by the adjustment of the interval d by the position adjustment mechanism 21.

Incidentally, a technical scope of the present invention is not one limited to each of the above embodiments, and it is possible to add various modifications in a scope not deviating from a gist of the present invention.

For example, although each of the above embodiments is the energy dispersive fluorescent X-ray analysis apparatus, there may be applied to other analysis system, e.g., a wavelength dispersive fluorescent X-ray analysis apparatus.

Further, in each of the above embodiments, although the X-ray from the X-ray tubular bulb 3 that is the X-ray source is used as the radiant ray to be irradiated to the sample, other radiant ray, e.g., electron beam or the like, may be adopted as the radiant ray to be irradiated.

Further, as the incident X-ray adjustment mechanism 7 that is an opening diameter alteration mechanism, although there is used the mechanism capable of altering by selecting any one of the X-ray incident holes 13 whose opening diameters differ, there may be one having, as other opening diameter alteration mechanism, one X-ray incident hole like, e.g., a diaphragm mechanism of camera, thereby being made such that the opening diameter of this X-ray incident hole can be altered to an arbitrary size.

What is claimed is:

1. An X-ray analysis apparatus comprising:
a radiation source configured to irradiate a radiant ray to a sample;
a radiant ray adjustment mechanism configured to adjust an intensity of the radiant ray;
an X-ray detector configured to detect a characteristic X-ray and a scattered X-ray, which are radiated from the sample, and output a signal including energy information of the characteristic X-ray and the scattered X-ray;
an analyzer configured to analyze the signal;
an incident X-ray adjustment mechanism disposed between the sample and the X-ray detector, and configured to adjust a total intensity of the characteristic X-ray and the scattered X-ray, which are entered to the X-ray detector; and
a control section configured to control the incident X-ray adjustment mechanism and the radiant ray adjustment mechanism such that the total intensity of the characteristic X-ray and the scattered X-ray, which are detected by the X-ray detector, is approximately a maximum obtainable X-ray intensity, and an intensity of the radiant ray becomes within a normal operation range of a radiant ray irradiation power of the radiation source.

2. An X-ray analysis apparatus according to claim 1, wherein the X-ray detector has a detection face receiving the characteristic X-ray and the scattered X-ray, and the incident X-ray adjustment mechanism is a collimator configured to adjust incident solid angles of the characteristic X-ray and the scattered X-ray in regard to the detection face.

3. An X-ray analysis apparatus according to claim 2, wherein the incident X-ray adjustment mechanism is an opening diameter alteration mechanism which has an X-ray incident hole allowing the characteristic X-ray and the scattered X-ray to pass through it and enter the detection face, and the opening diameter alteration mechanism configured to alter an opening diameter of the X-ray incident hole.

4. An X-ray analysis apparatus according to claim 2, wherein the incident X-ray adjustment mechanism is an opening diameter alteration mechanism which has plurality of X-ray incident holes whose opening diameters mutually differ, and arbitrarily disposes any one of the X-ray incident holes between the detection face and the sample.

5. An X-ray analysis apparatus according to claim 3, wherein the incident X-ray adjustment mechanism has a position adjustment mechanism configured to adjust a distance between the X-ray incident hole and the detection face.

6. An X-ray analysis method comprising:
irradiating a radiant ray to a sample from a radiation source at a intensity previously set for a rough measurement;
detecting, by an X-ray detector, a rough measurement value that is a total intensity of a characteristic X-ray and a scattered X-ray, which are radiated from the sample;
performing a main measurement by adjusting, based on the intensity of the radiant ray previously set for the rough measurement and the rough measurement value, the intensity of the radiant ray, using a radiant ray adjustment mechanism, such that the total intensity of the characteristic X-ray and the scattered X-ray, which are detected by the X-ray detector, is approximately a maximum obtainable X-ray intensity and an intensity of the radiant ray becomes within a normal operation range of a radiant ray irradiation power of the radiation source, and by adjusting a total intensity of the characteristic X-ray and the scattered X-ray, which are entered to the X-ray detector, using an incident X-ray adjustment mechanism disposed between the sample and the X-ray detector;

outputting a signal including energy information of the characteristic X-ray and the scattered X-ray, that the X-ray detector obtains in the main measurement; and analyzing the signal by an analyzer.

* * * * *